United States Patent [19]
Lakowicz et al.

[11] Patent Number: 5,648,269
[45] Date of Patent: Jul. 15, 1997

[54] PH AND PCO$_2$ SENSING BY LUMINESCENT LIFETIMES AND ENERGY TRANSFER

[75] Inventors: Joseph R. Lakowicz, 9142 Emerson's Reach, Columbia, Md. 21045; Henry K. Szmacinski, Baltimore, Md.

[73] Assignee: Joseph R. Lakowicz, Ellicott City, Md.

[21] Appl. No.: 403,554

[22] Filed: Mar. 14, 1995

Related U.S. Application Data

[63] Continuation of Ser. No. 186,883, Jan. 26, 1994, abandoned, which is a continuation of Ser. No. 822,234, Jan. 17, 1992, abandoned, which is a continuation-in-part of Ser. No. 694,282, May 3, 1991, abandoned.

[51] Int. Cl.$^6$ .................................................. G01N 21/64
[52] U.S. Cl. .............................. 436/68; 436/133; 436/163; 436/172
[58] Field of Search .............................. 436/68, 133, 163, 436/166, 172; 250/459.1

[56] References Cited

U.S. PATENT DOCUMENTS

| | | | |
|---|---|---|---|
| 4,854,321 | 8/1989 | Boiarski | 128/634 |
| 5,037,615 | 8/1991 | Kane | 128/634 |
| 5,127,405 | 7/1992 | Alcala et al. | 128/634 |

FOREIGN PATENT DOCUMENTS

| | | |
|---|---|---|
| 0397641 | 11/1990 | European Pat. Off. . |
| 0442276 | 8/1991 | European Pat. Off. . |

OTHER PUBLICATIONS

"Applications of Fluorescence in the Biomedical Sciences" Lakowicz, J.R., Alan R. Liss, Inc., pp. 29–67 (1986).
Jordan, D.M. et al. "Physiological pH Fiber–Optic Chemical Sensor Based on Energy Transfer", Analytical Chemistry, vol. 59, pp. 437–439 (1987).
Lakowicz 'Principles of Fluorescence Spectrocopy' Plenum Press, 1983.

*Primary Examiner*—Jeffrey Snay
*Attorney, Agent, or Firm*—Rothwell, Figg, Ernst & Kurz

[57] ABSTRACT

A method for determining pH or pCO$_2$ using luminescent lifetimes and energy transfer in which an energy transfer donor-acceptor pair is exposed to a sample to be analyzed, the donor of the donor-acceptor pair being photoluminescent and the acceptor of the donor-acceptor pair being sensitive to the pH or pCO$_2$ of the sample. One or both of the donor-acceptor pair may be bound to a carrier. The sample is irradiated and the resultant emission detected. By measuring the apparent luminescent lifetime, the pH or pCO$_2$ of the sample can be determined.

7 Claims, 13 Drawing Sheets

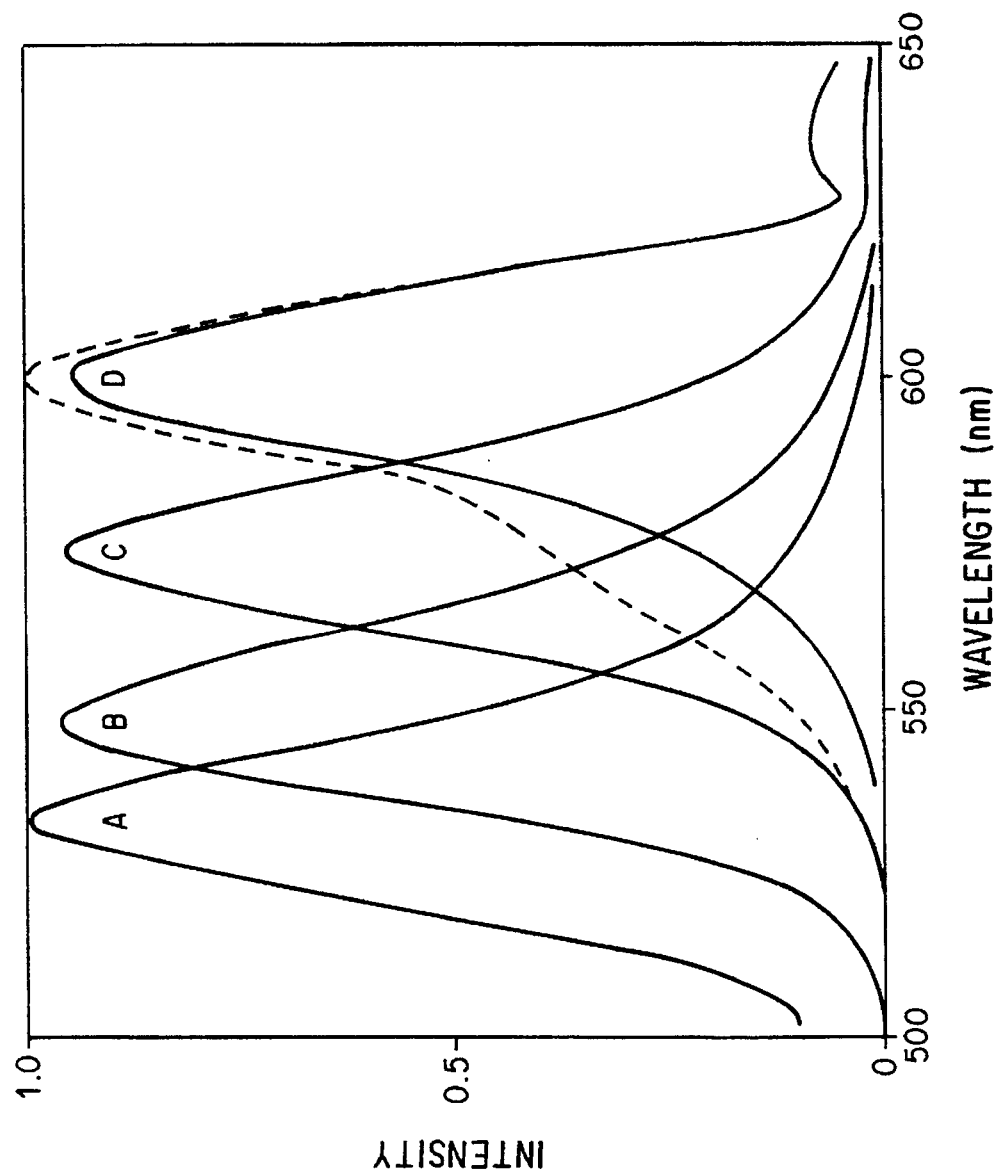

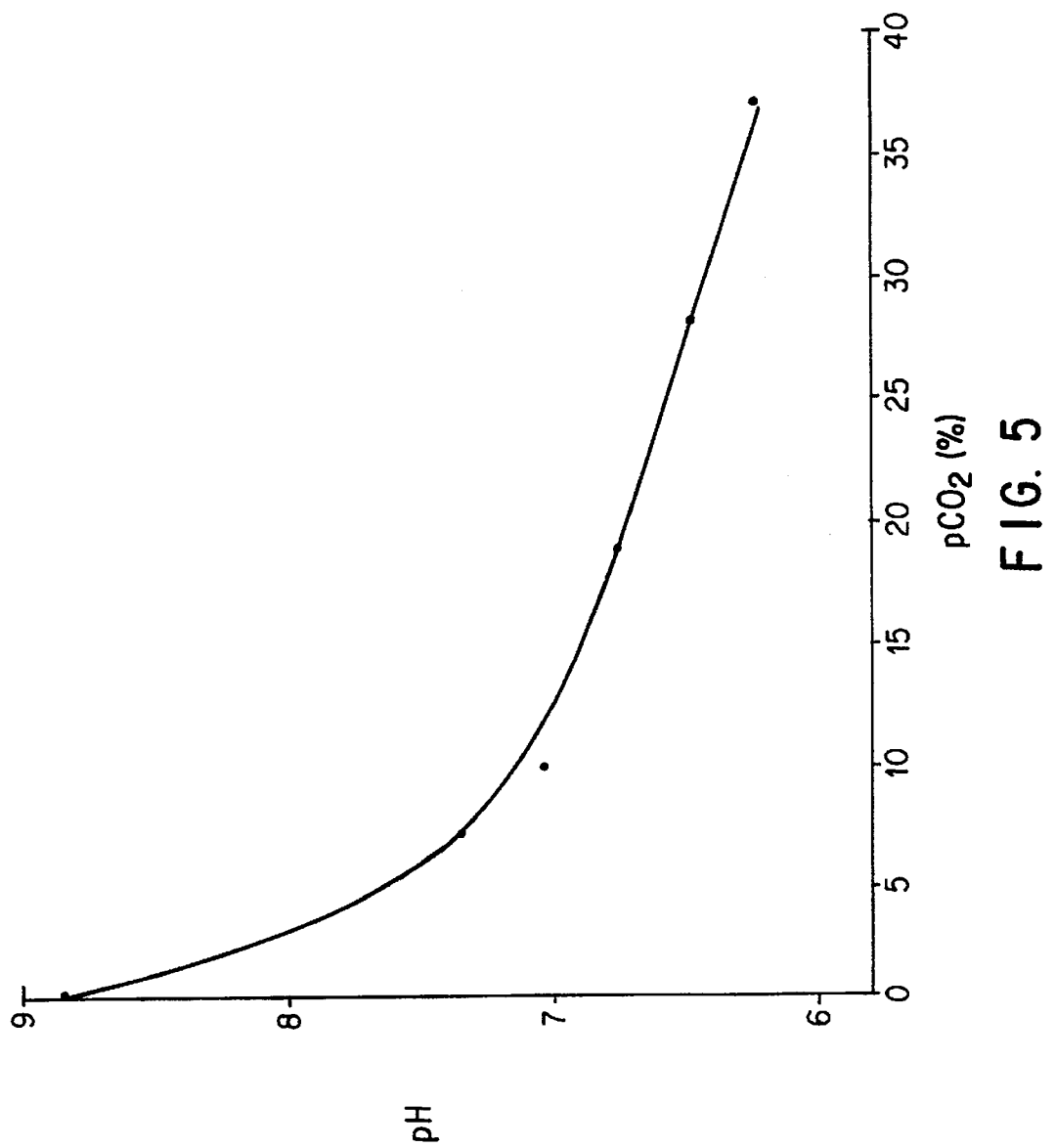

PH AND PCO$_2$ SENSING BY LUMINESCENT LIFETIMES AND ENERGY TRANSFER

CROSS REFERENCE TO RELATED APPLICATIONS

This is a continuation application of U.S. Ser. No. 08/186883, filed Jan. 26, 1994, now abandoned, which is a continuation of application of U.S. Ser. No. 07/822234, filed Jan. 17, 1992, now abandoned, which is a continuation-in-part of U.S. Ser. No. 07/694282, filed May, 3, 1991, now abandoned.

FIELD OF THE INVENTION

The present invention relates to a method of determining pH and pCO$_2$ and, more particularly, to a method of determining pH and pCO$_2$ using luminescence lifetimes, e.g. fluorescence or phosphorescence, and energy transfer.

BACKGROUND OF THE INVENTION

Determination of pH and pCO$_2$ has a wide variety of clinical and analytical applications. Recently, it has been discovered that it is possible to determine pH and pCO$_2$ of a sample using fluorescent intensity measurements. See, for example, Yuan and Walt, "pH-Dependent Fluorescence of Merocyanine-Eosin-Labeled Water-Soluble Polymers", *Macromolecules* 23, 4611–15 (1990). However, fluorescent intensity measurements are disadvantageous in that they can be inaccurate and/or imprecise in view of photo-bleaching, light scattering off the tissues in the case of in vivo clinical work and high-absorbance by the sample.

Also, although it is generally known that the fluorescent lifetime changes, as opposed to the intensity, of a fluorescent emission can be measured, there is no suggestion in the prior art of fluorescent indicator molecules which would exhibit suitable lifetime changes to allow for the measurement of pH and pCO$_2$ using fluorescent lifetime measurements. Moreover, it is difficult to obtain the desired spectral properties, sensitivity to pH or pCO$_2$, and the desired pK (dissociation constant) all within a single chromophore.

SUMMARY OF THE INVENTION

The present invention overcomes the above difficulties by providing a method for determining pH and pCO$_2$ using luminescent lifetimes and energy transfer. According to the method of the invention, an energy transfer donor-acceptor pair is exposed to a sample to be analyzed, the donor being photoluminescent and the acceptor being sensitive to the pH or pCO$_2$ of the sample. The energy transfer process depends, in part, on the value of the spectral overlap integral, which, in turn, depends on the change in extinction coefficient or shift in absorbance of the acceptor caused by the hydrogen ion or carbon dioxide concentration of the sample. In this way, the energy transfer between the donor and acceptor is affected by the pH or pCO$_2$ of the sample. Alternatively, the donor could be sensitive to the sample, for example exhibiting a fluorescence shift, in response to pH or pCO$_2$. This shift will result in a different spectral overlap, a different rate of energy transfer, and hence lifetime of the donor.

According to the invention, the sample is then illuminated and the resultant emission detected. As mentioned above, the donor is luminescent, and the effect of the pH or pCO$_2$ on the energy transfer causes a change in the apparent luminescent lifetime. By measuring the apparent luminescent lifetime, for example, by phase-modulation fluorometry or time-resolved fluorometry, the pH or pCO$_2$ of the sample can be determined.

BRIEF DESCRIPTION OF THE DRAWINGS

FIG. 2 is a graphical representation of the emission spectra of the donors shown in FIG. 1;

FIG. 5 is a graphical representation of pH versus concentration of carbon dioxide;

DETAILED DESCRIPTION OF THE PREFERRED EMBODIMENTS

According to the method of the invention, an energy transfer donor-acceptor pair is exposed to a sample to be analyzed. For the purposes of the invention, "sample" is to be broadly construed to include any compounds, surfaces, solutions, emulsions, suspensions, mixtures, cell cultures, fermentation cultures, cells, tissues, secretions and/or derivatives or extracts thereof. Measurements in accordance with the method of the invention can be taken in vitro, in vivo and in situ.

Figure 1:
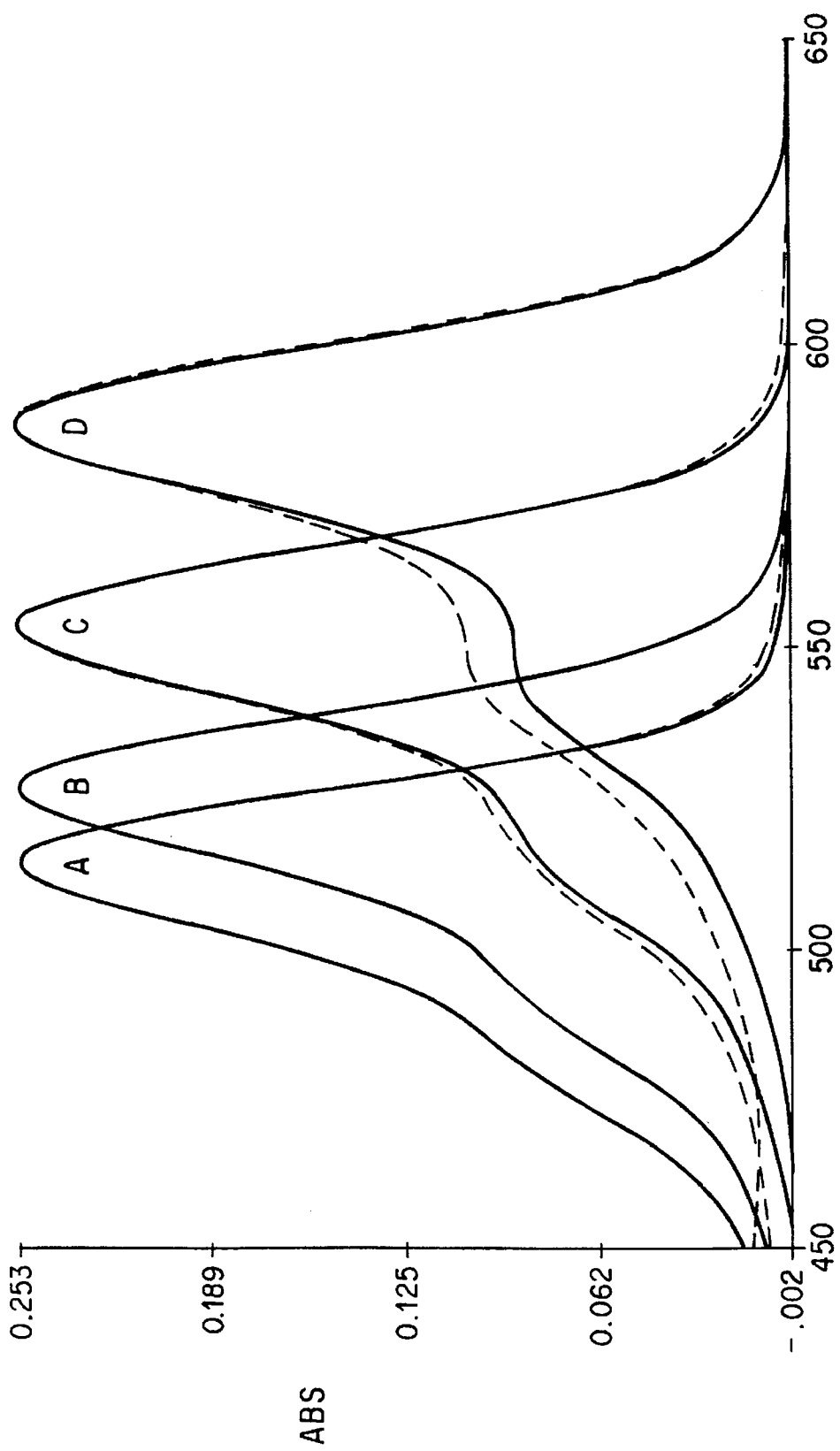
FIG. 1 is a graphical representation of the absorption spectra of certain fluorescent donors in accordance with the present invention.

According to the invention, the donor of each donor-acceptor pair is photoluminescent. Suitable fluorescent donors include eosin, rhodamine 6G, rhodamine B and Texas Red Hydrazide. The absorption spectra of these donors in 40 mM bicarbonate solution at room temperature are shown in FIG. 1. As can be seen from FIG. 1, all donors can be excited at 543 nm, which allows the use of a HeNe laser as the light source, and the absorption spectra are, for the most part, independent of carbon dioxide concentration. The uncorrected emission spectra of these donors are shown in FIG. 2.

It is also contemplated that longer lived fluorophores, such as lanthanides and metal-ligand complexes, may be suitable as donors. The use of longer-lived fluorophores may be particularly useful in clinical measurements of blood samples because they provide for suppression of autofluorescence from tissue. It is also contemplated that longer wavelength absorbing donors may be used, which would allow the use of inexpensive laser diode light sources.

Figure 3:
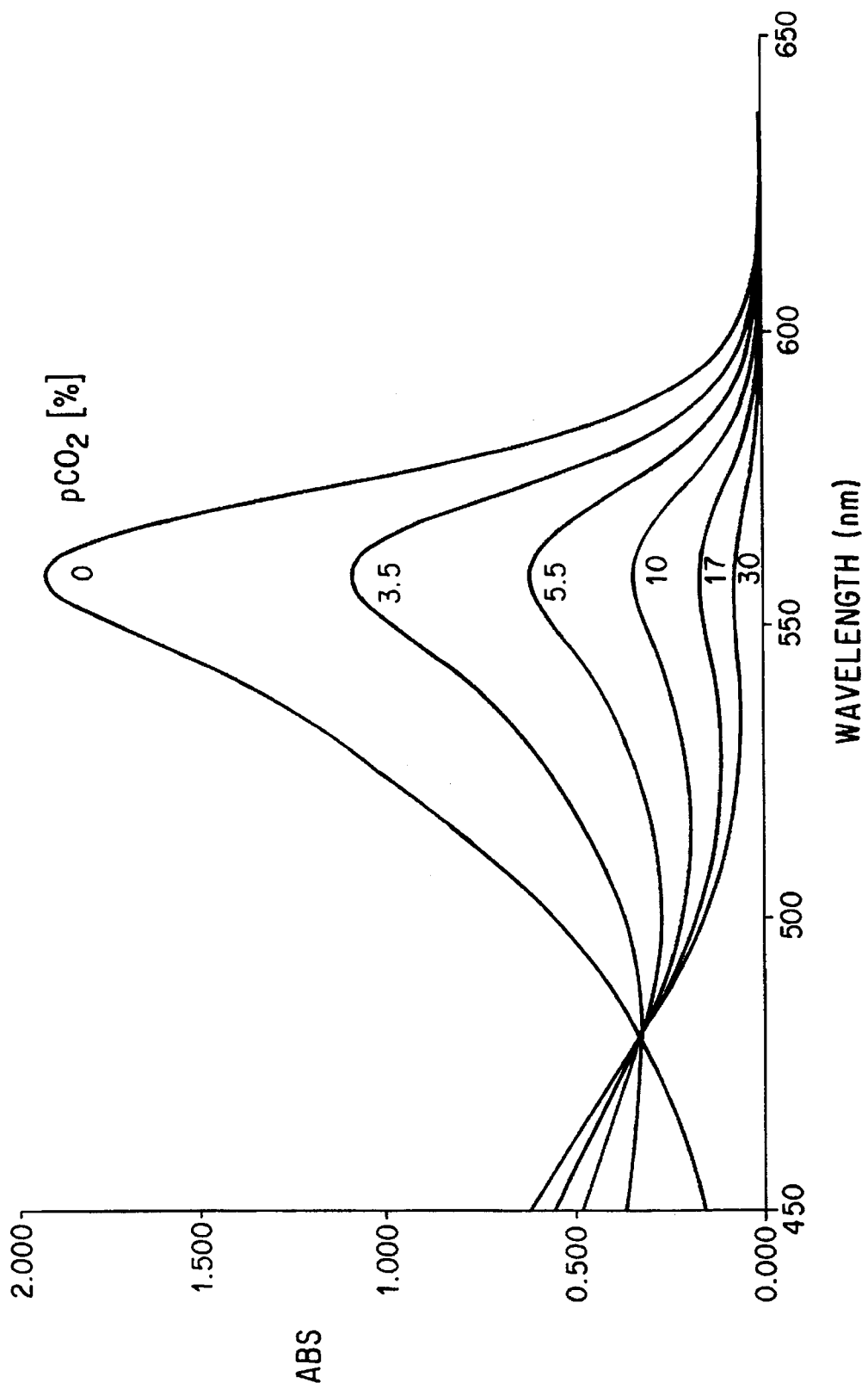
FIG. 3 is a graphical representation of the carbon dioxide-dependent absorption spectra of an acceptor, Phenol Red, in accordance with the present invention.
Figure 4:
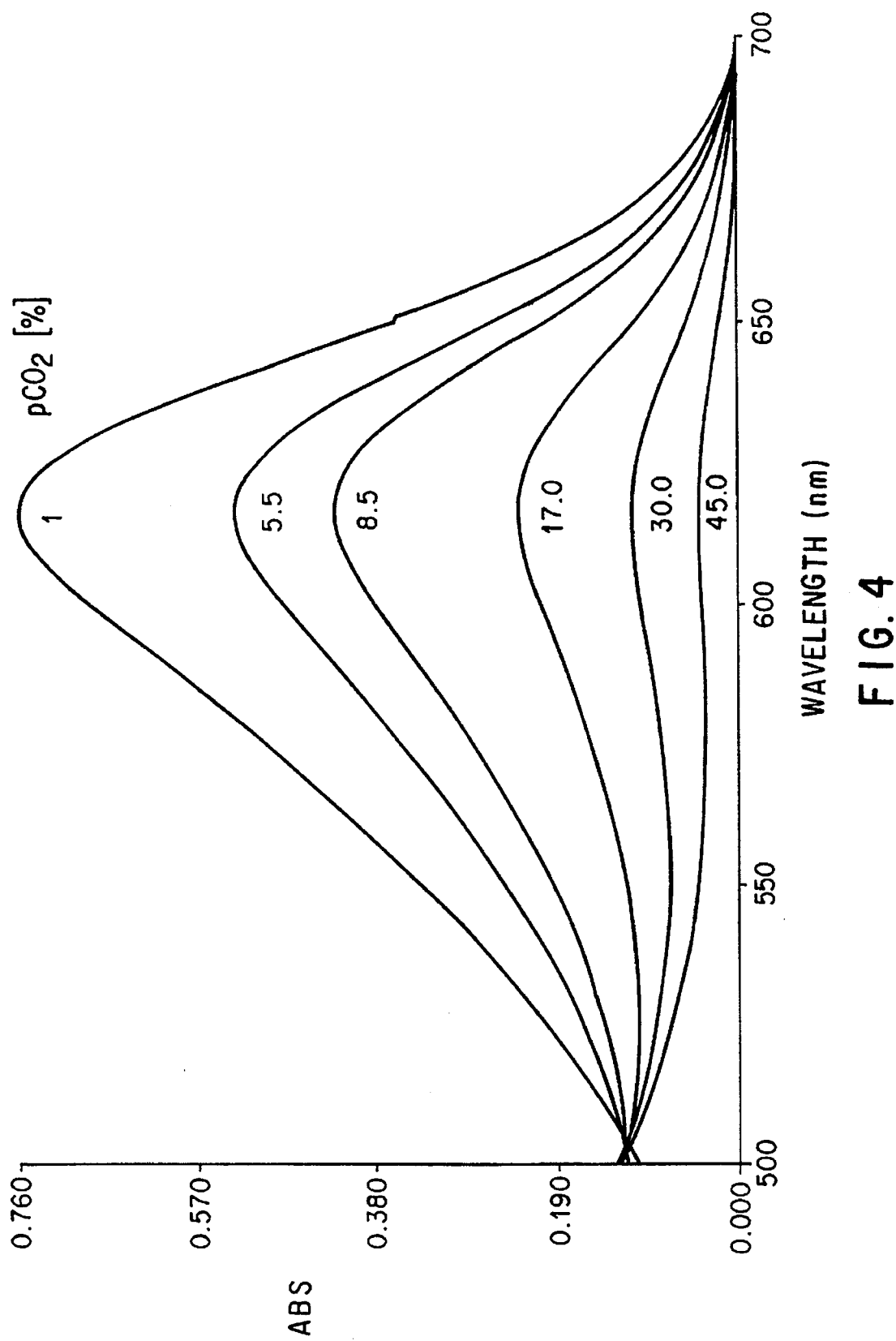
FIG. 4 is a graphical representation of the carbon dioxide-dependent absorption spectra of another acceptor, Bromothymol Blue, in accordance with the present invention.

Also according to the invention, the acceptor of each donor-acceptor pair is sensitive to changes in pH or $pCO_2$. It is contemplated that suitable acceptors may include Phenol Red, water-soluble Phenol Red and Bromothymol Blue. The carbon dioxide-dependent absorption spectra of Phenol Red is shown in FIG. 3. As can be seen from FIG. 3, the absorption spectra of Phenol Red at 560 nm decreases with increasing carbon dioxide concentration. Applicants found that the absorption spectra of Phenol Red make it suitable as an acceptor for the donors Eosin, Rhodamine 6G, Rhodamine B and Texas Red, each with a different Forster distance. The carbon dioxide-dependent absorption spectra of Bromothymol Blue are shown in FIG. 4. As can be seen from FIG. 4, the longer wavelength absorption spectra of Bromothymol Blue make it suitable for the longer wavelength emitting donors. The donor and acceptor may be linked via a spacer and may be present in a known ratio.

According to the invention, one or both of the donor-acceptor pair may be bound to a carrier, with covalent bonding between the donor/acceptor and carrier being acceptable and even desirable in some cases. Polymeric carriers, such as hydrogels, may be especially useful in some applications.

The method of the invention further includes the step of illuminating the sample with any suitable radiation source, such as a continuous wave (CW) laser, or a laser diode or the like. Light sources particularly suitable for use in the methods of the present invention include green helium-neon lasers. For measurement of lifetimes, the light sources must be intensity modulated at an appropriate frequency, or be pulsed with a suitably short pulse width. The resultant emission may be filtered using, for example, a Corning 2-73 filter, and is then detected.

In accordance with the present invention, energy transfer occurs between the donor and the acceptor. According to Förster resonance energy transfer theory, the energy transfer process depends on the quantum yield of the donor, the overlapping of the emission spectrum of the donor with the absorption spectrum of the acceptor (i.e., the spectral overlap integral), and the relative distance and orientation between the donor and the acceptor. The spectral overlap integral, in turn, depends on the reduction in extinction coefficient or shift in absorbance of the acceptor caused by the hydrogen ion or carbon dioxide concentration of the sample. In this way, the energy transfer between the donor and acceptor is affected by the pH or $pCO_2$ of the sample.

Applicants note that it is known to measure pH and $pCO_2$ by adding a luminescent ligand to the sample to be analyzed in the form of a photoluminescent probe having intrinsic analyte-induced luminescent lifetime changes. See copending U.S. application Ser. No. 07/694,282 to Lakowicz et al., filed May 3, 1991, now abandoned, the contents of which are incorporated herein by reference. In a preferred embodiment of the present invention, the intensity of the excitation radiation is modulated at a particular modulation frequency and the lifetime determined using known phase-modulation, i.e., frequency-domain, techniques. Alternatively, a pulsed radiation source may be used and the lifetime of the sample determined using known time-resolved methods. Both phase-modulation and time-resolved fluorometry methods are well known in the prior art, see Lakowicz, *Principles of Fluorescence Spectroscopy*, Plenum Press, 1983, Chapter 3. However, current instrumentation renders the phase-modulation method more expedient. For the sake of conciseness, only the phase-modulation method will be discussed further herein, but it is understood that these same principles generally apply to time-resolved measurements.

Figure 10:
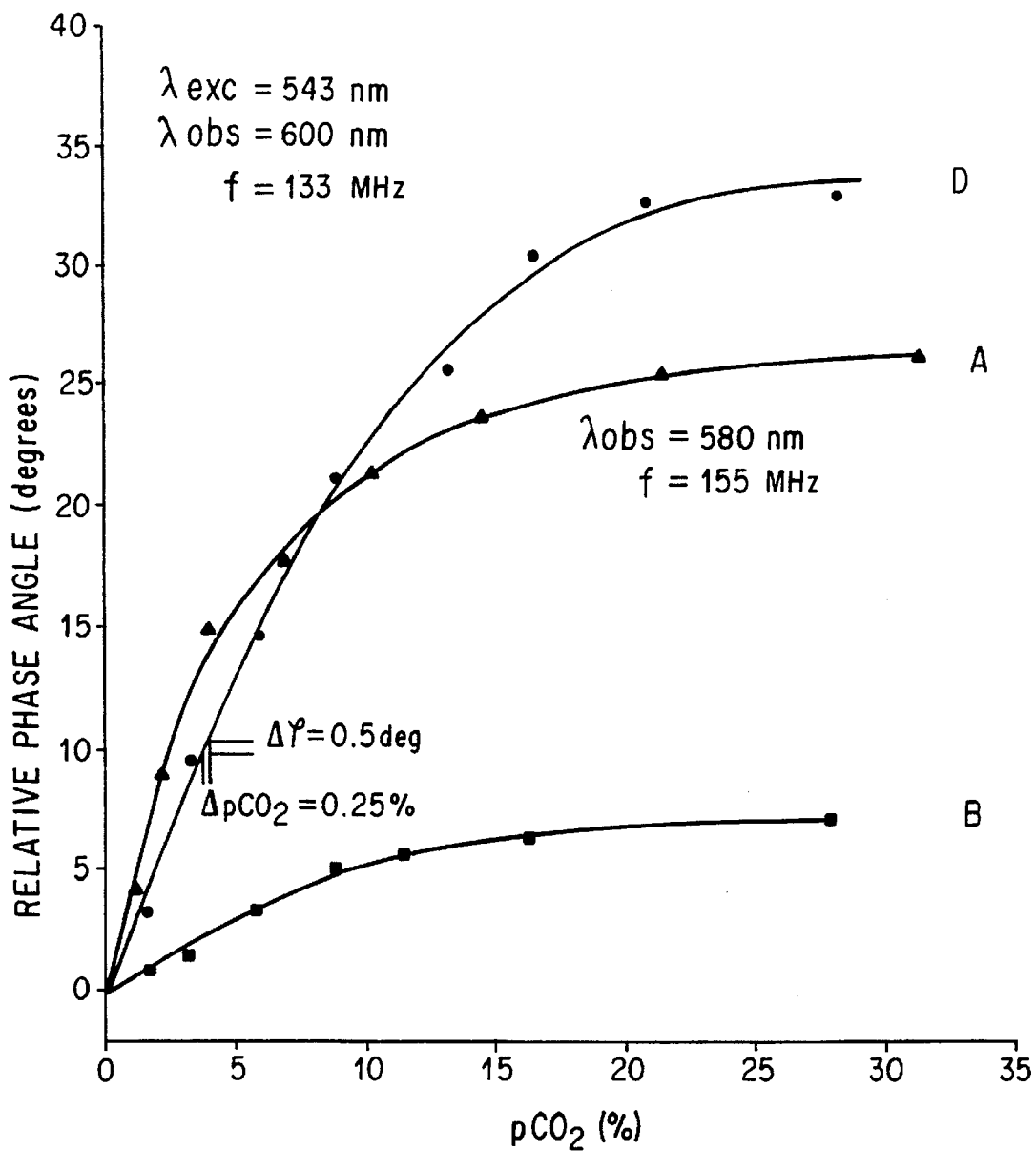
FIG. 10 is a graphical representation of concentration of carbon dioxide versus relative phase angle for the donor-acceptor pairs Eosin-Phenol Red, Rhodamine 6G-Phenol Red, and Texas Red-Bromothymol Blue.
Figure 11:
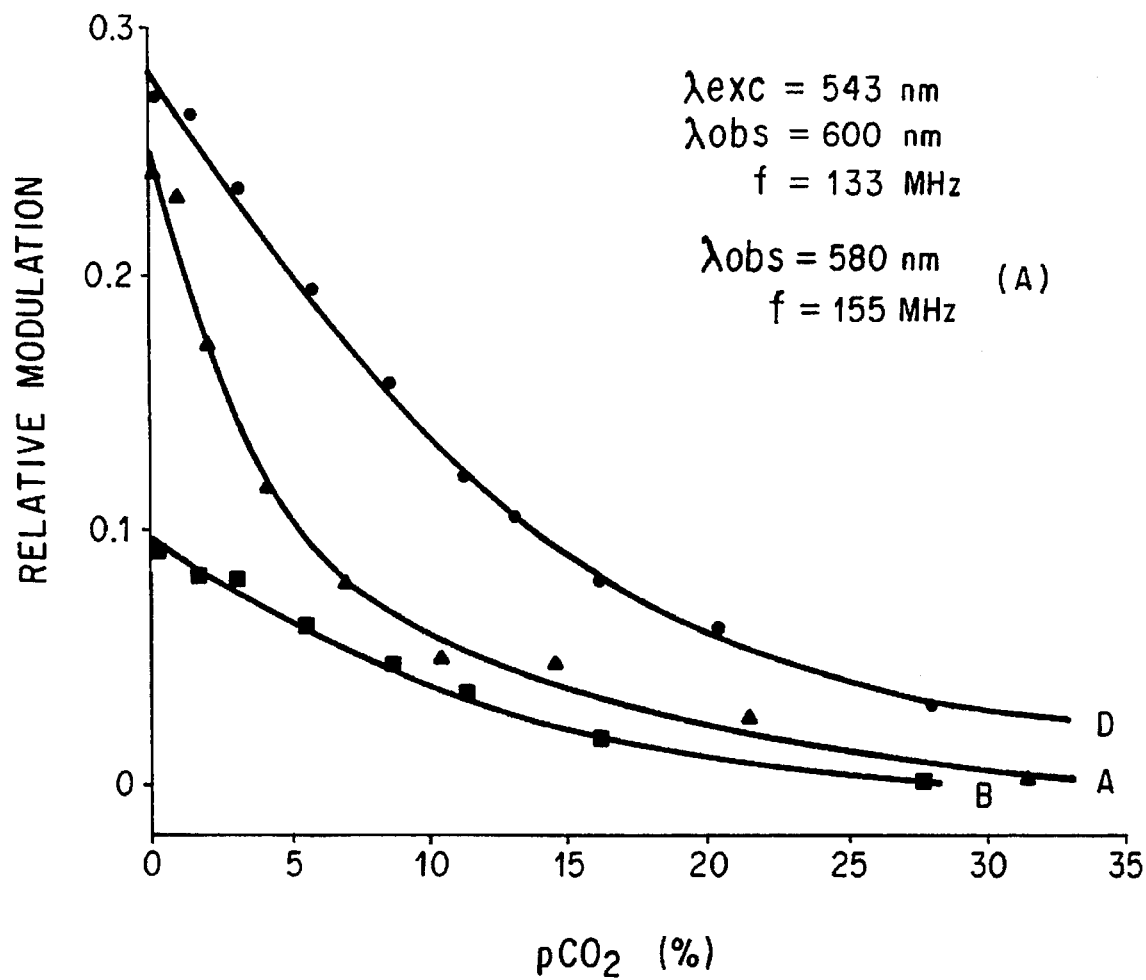
FIG. 11 is a graphical representation of concentration of carbon dioxide versus relative modulation factor for the donor-acceptor pairs Eosin-Phenol Red, Rhodamine 6G-Phenol Red, and Texas Red-Bromothymol Blue.

When the sample is excited with radiation whose intensity is modulated, for example, in a sinusoidal manner, the time lag between absorption and emission causes the emission to be delayed in phase and demodulated relative to the excitation radiation. This phase shift and the corresponding demodulation factor m are used to measure and calculate the photoluminescent lifetime based on well known formulae. See, Lakowicz, supra. This, in turn, can be used to calculate the concentration of carbon dioxide, as shown in FIGS. 10 and 11 and described in more detail below. As shown in FIG. 5, the concentration of hydrogen ions can be determined from the carbon dioxide concentration and vice versa. Alternatively, it is contemplated that a suitable pH-sensitive donor or acceptor could be used and the conversion step eliminated. For a specific example of instrumentation useful in conjunction with the present invention, see copending U.S. application Ser. No. 07/694,282 referred to above.

EXAMPLE 1

Donor-acceptor pairs were prepared using the donor Eosin (concentration $5 \times 10^{-4}$ mol/l) and the acceptor Phenol Red (concentrations $4 \times 10^{-3}$ mol/l and $6 \times 10^{-3}$ mol/l). In each case, the donor and acceptor were in hydrogel, encased in a carbon dioxide-permeable silicon membrane.

Figure 6A:
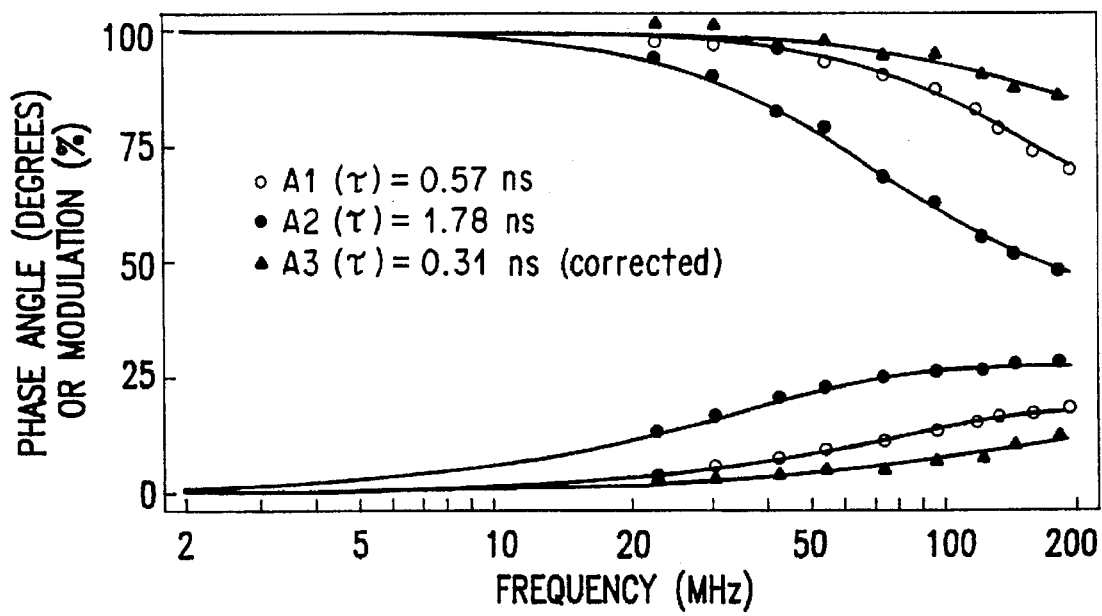
FIGS. 6A–6C are a graphical representation showing uncorrected and corrected modulation frequency versus phase angle and modulation factor for the donor-acceptor pair Eosin-Phenol Red.
Figure 6B:
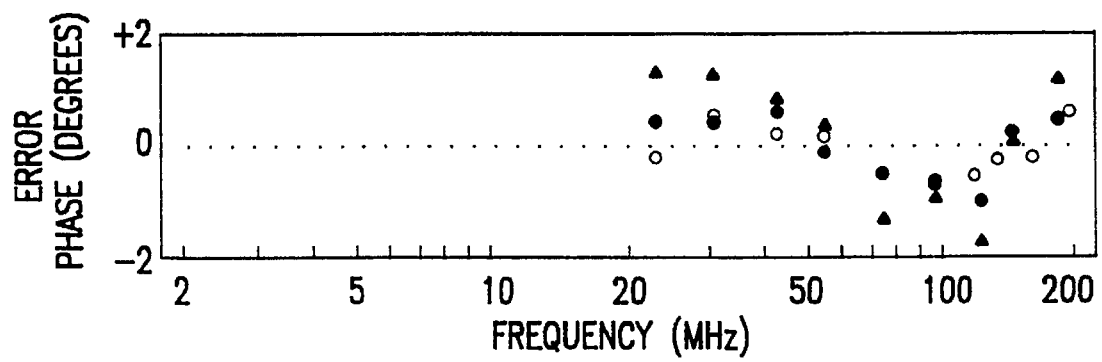
Figure 6C:
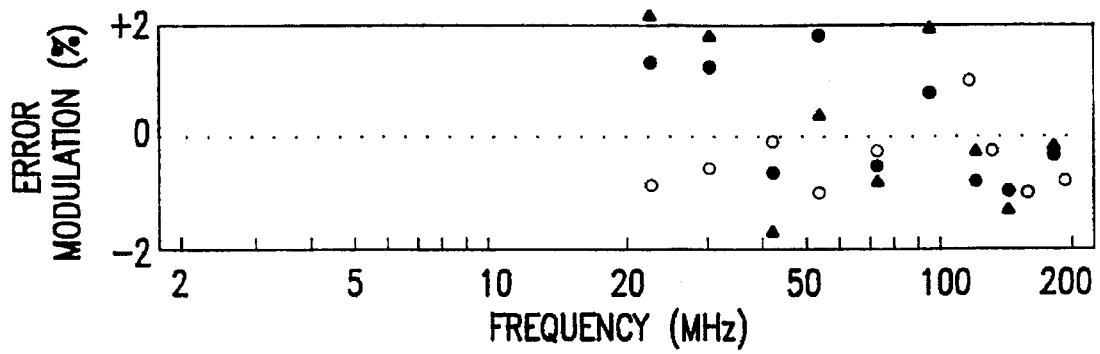

The frequency response of the donor alone and the donor with the lower acceptor concentration were measured, as shown in FIG. 6. All frequency responses were measured with 560 nm excitation using an R6G dye laser and a 600 nm interference filter for emission at 25° C. The samples were maintained with 100% humidity.

As can be seen in FIG. 6, as the frequency increases, the phase angle increases and the modulation factor decreases. In this figure, the measured frequency-response of the donor with the acceptor (A-2) was corrected for a long-lived component, to obtain the corrected frequency-response (A-3).

The donor was excited with a green acousto-optically modulated HeNe laser. The carbon dioxide concentration responses shown in FIGS. 10 and 11 were measured at a selected modulation frequency of 133 MHz. Samples were equilibrated with $CO_2/N_2$ mixtures from a two-tube gas blender with a high accuracy measuring valve.

Figure 12:
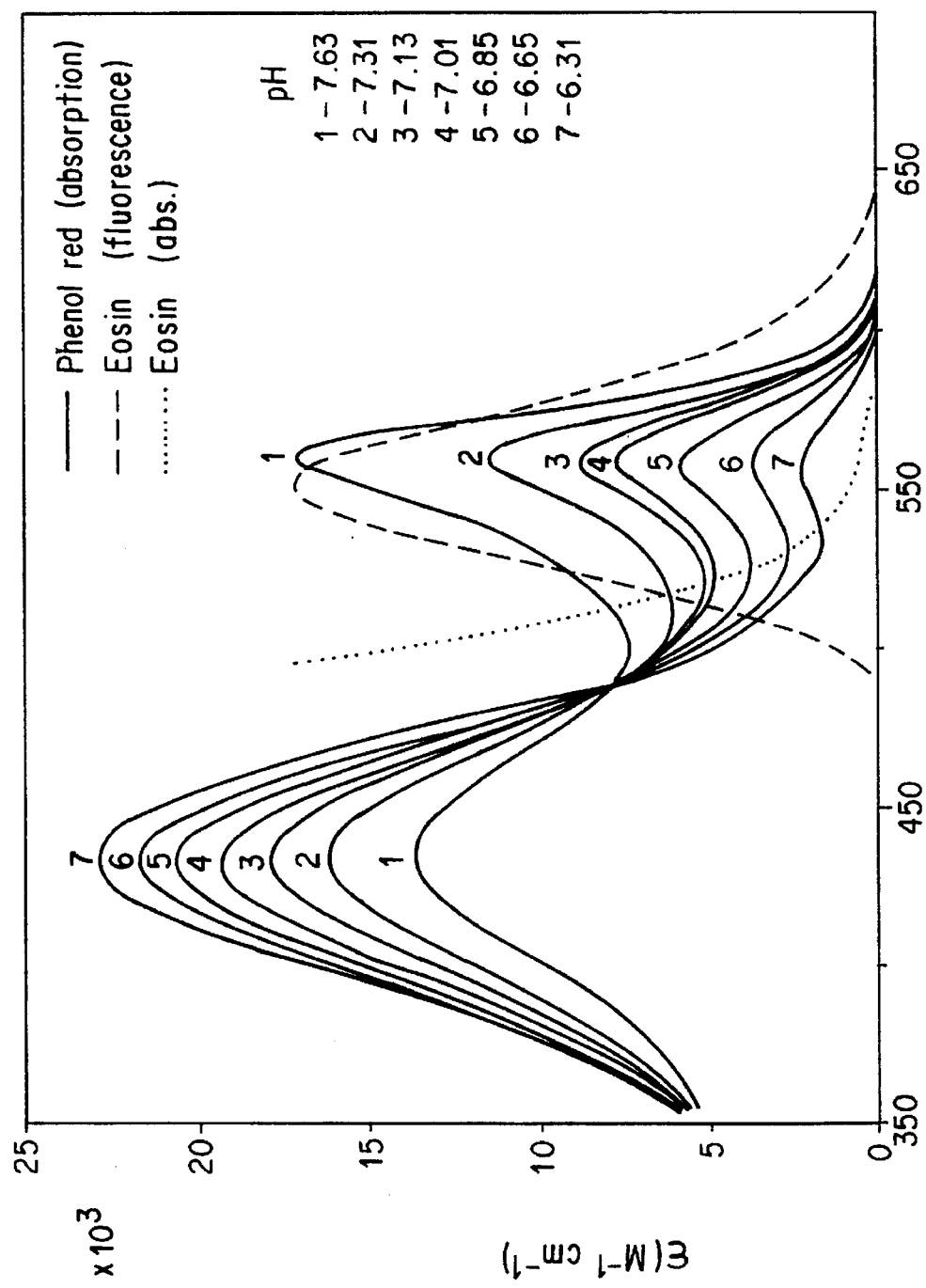
FIG. 12 shows the overlap of the donor and acceptor spectra for the Eosin-Phenol Red pair.
Figure 13:
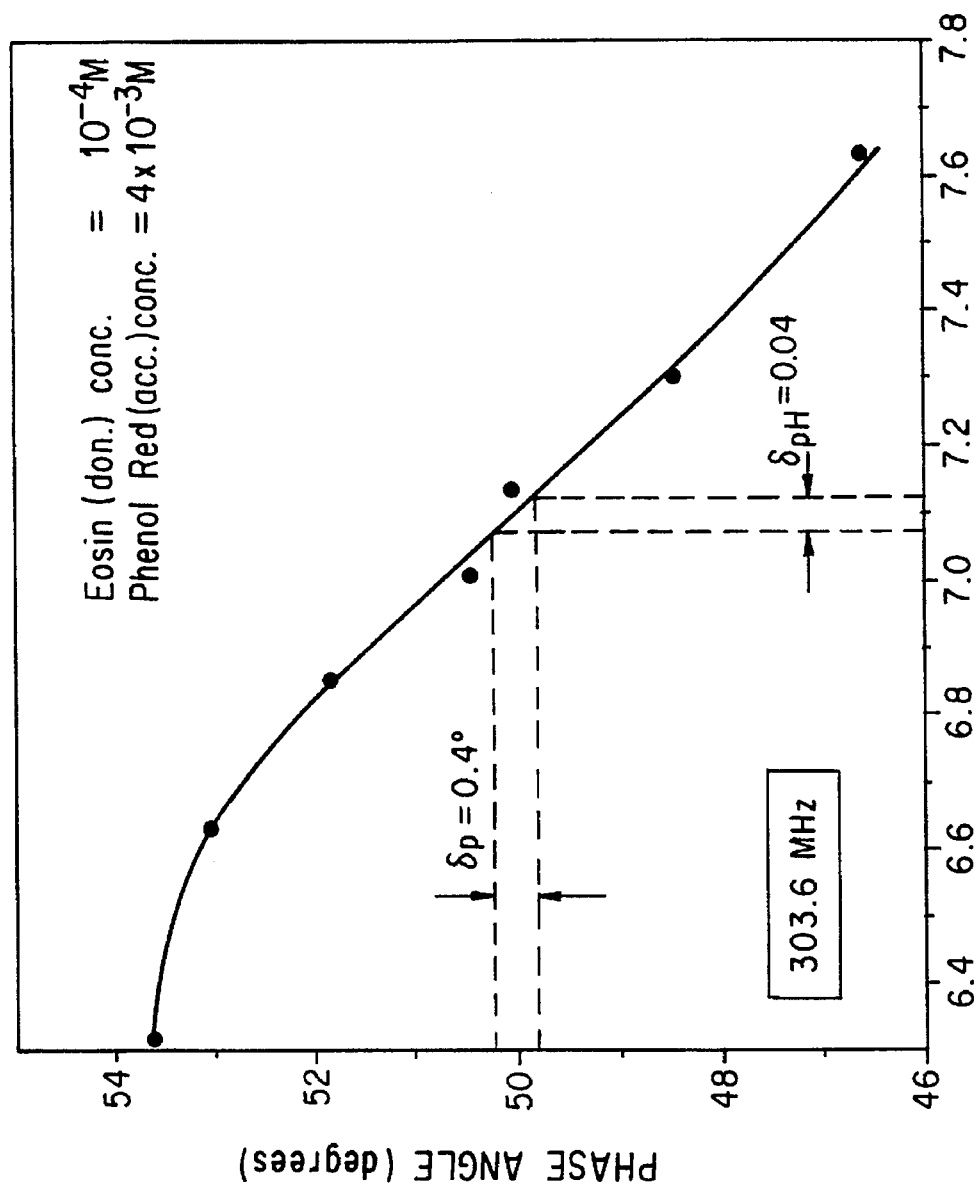
FIG. 13 shows the relationship between phase angle and pH for the Eosin-Phenol Red pair.

As can be seen from FIGS. 10 and 11, for the donor-acceptor pair Eosin-Phenol Red, as the concentration of carbon dioxide increases, the relative phase angle also increases, while the modulation factor decreases. FIG. 12 shows the overlap of the emission spectra of the donor eosin with the absorption spectra of the acceptor phenol red. FIG. 13 shows the relationship of phase angle and pH for the eosin-phenol red system.

EXAMPLE 2

Donor-acceptor pairs were prepared using the donor Rhodamine 6G (concentration $5 \times 10^{-4}$ mol/l) and the acceptor Phenol Red (concentrations $4 \times 10^{-3}$ mol/l and $6 \times 10^{-3}$ mol/l). As in Example 1, the donor and acceptor were in hydrogel, encased in a carbon dioxide-permeable silicon membrane.

Figure 7A:
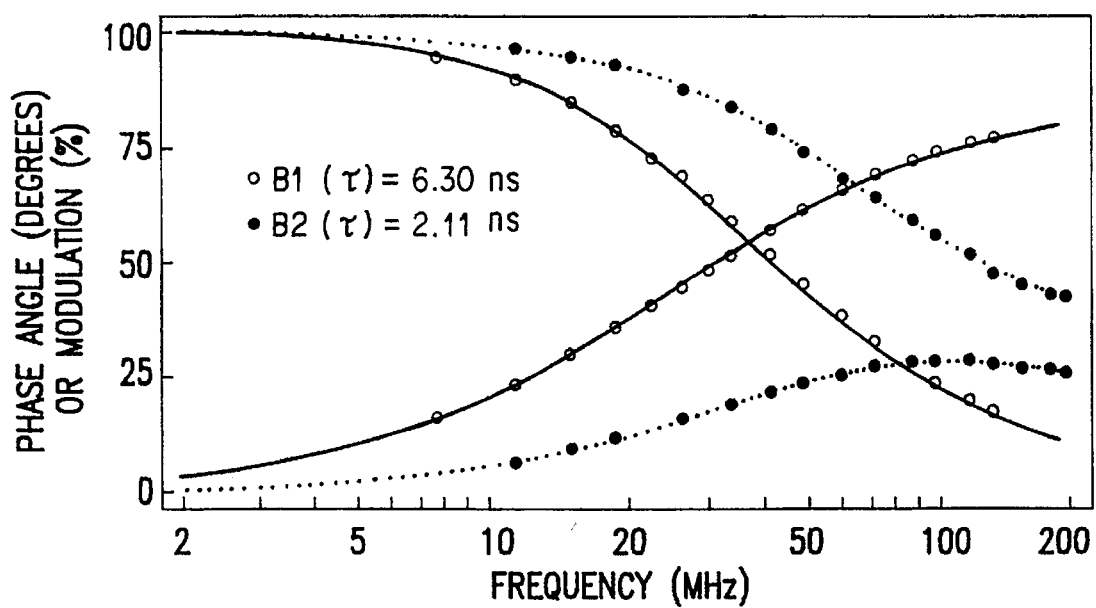
FIGS. 7A–7C are a graphical representation of modulation frequency versus phase angle and modulation factor for the donor-acceptor pair Rhodamine 6G-Phenol Red.
Figure 7B:
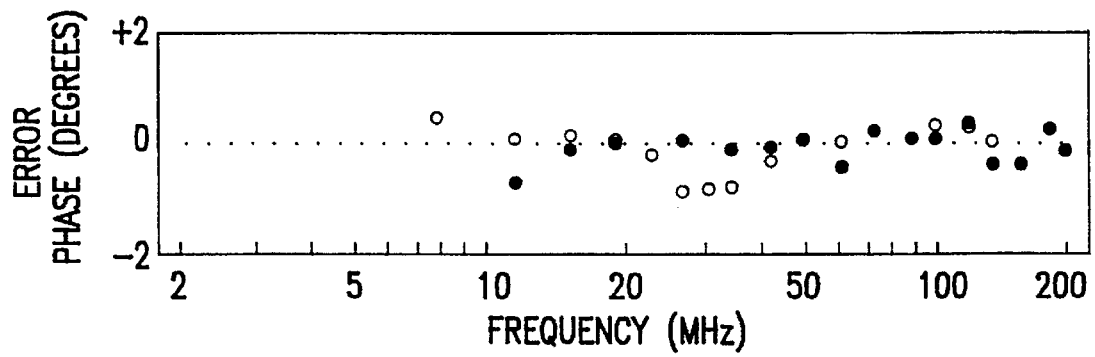
Figure 7C:
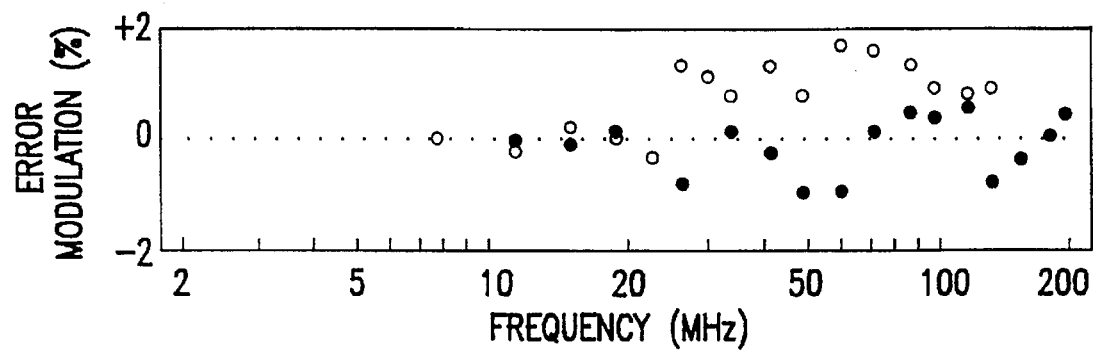

The frequency response of the donor alone and the donor with the lower acceptor concentration were measured, as shown in FIG. 7. As in Example 1, the frequency responses were measured with 560 nm excitation using an R6G dye laser and a 600 nm interference filter for emission at 25° C. The samples were maintained with 100% humidity.

As can be seen in FIG. 7, as the frequency increases, the phase angle increases and the modulation factor decreases, although somewhat more dramatically than in Example 1. Interestingly, the acceptor has a significant effect on the frequency response of the donor.

As in Example 1, the donor was excited with a green acousto-optically modulated HeNe laser. The carbon dioxide concentration responses shown in FIGS. 10 and 11 were measured at a selected frequency of 133 MHz. Samples were equilibrated with $CO_2/N_2$ mixtures from a two-tube gas blender with a high accuracy measuring valve.

As can be seen from FIGS. 10 and 11, for the donor-acceptor pair Rhodamine 6G-Phenol Red, as the concentration of carbon dioxide increases, the relative phase angle also increases, while the modulation factor decreases, although to a lesser degree than in Example 1.

EXAMPLE 3

Donor-acceptor pairs were prepared using the donor Rhodamine B (concentration $1\times10^{-4}$ mol/l) and the acceptor Phenol Red (concentrations $6\times10^{-3}$ mol/l and $9\times10^{-3}$ mol/l). As in the previous examples, the donor and acceptor were in hydrogel, encased in a carbon dioxide-permeable silicon membrane.

Figure 8A:
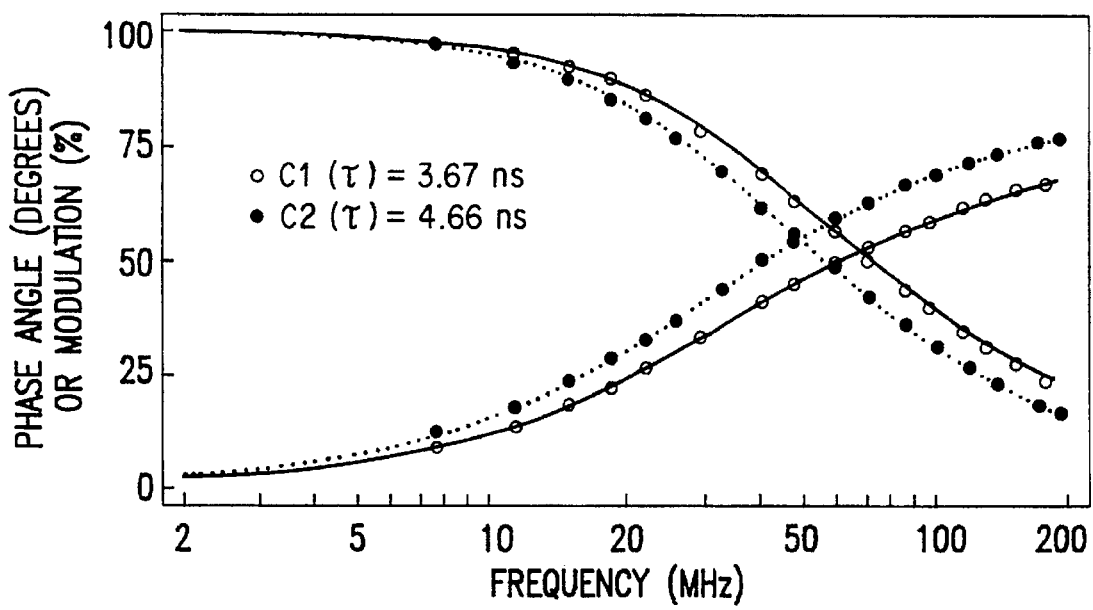
FIGS. 8A–8C are a graphical representation of modulation frequency versus phase angle and modulation factor for the donor-acceptor pair Rhodamine B-Phenol Red.
Figure 8B:
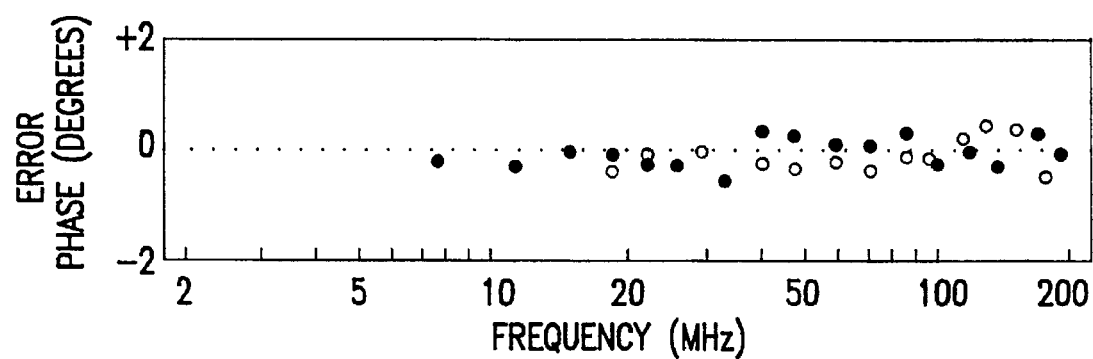
Figure 8C:
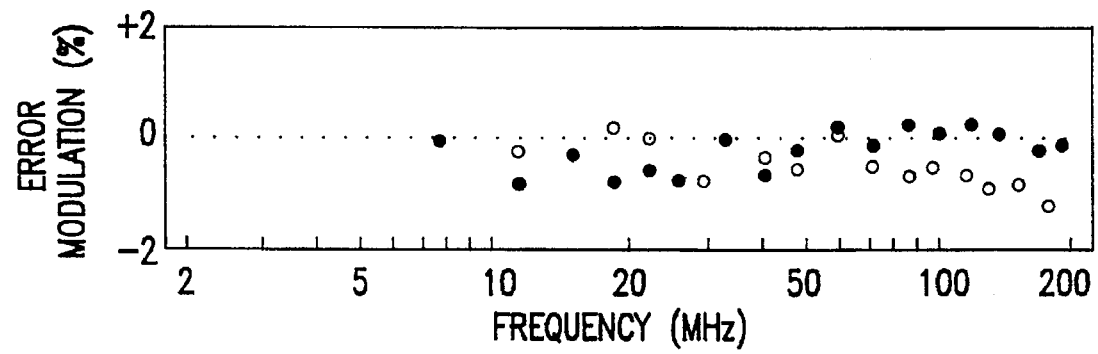

The frequency response of the donor alone and the donor with the lower acceptor concentration were measured, as shown in FIG. 8. As in the previous examples, the frequency responses were measured with 560 nm excitation using an R6G dye laser and a 600 nm interference filter for emission at 25° C. The samples were maintained with 100% humidity.

As can be seen in FIG. 8, as the frequency increases, the phase angle increases and the modulation factor decreases. The effect of the acceptor on the frequency response of the donor (C-2) is surprising because it is in the direction opposite to the expected result. This fact may be attributed to the donor being absorbed by the silicon in which it is encased, which was visually apparent.

The carbon dioxide-dependent phase angles and modulation factors were not measured for this donor-acceptor pair.

EXAMPLE 4

Donor-acceptor pairs were prepared using the donor Texas Red (concentration $3\times10^{-5}$ mol/l) and the acceptor Bromothymol Blue (concentrations $2\times10^{-3}$ mol/l and $4\times10^{-3}$ mol/l). As in the previous examples, the donor and acceptor were in hydrogel, encased in a carbon dioxide-permeable silicon membrane.

Figure 9A:
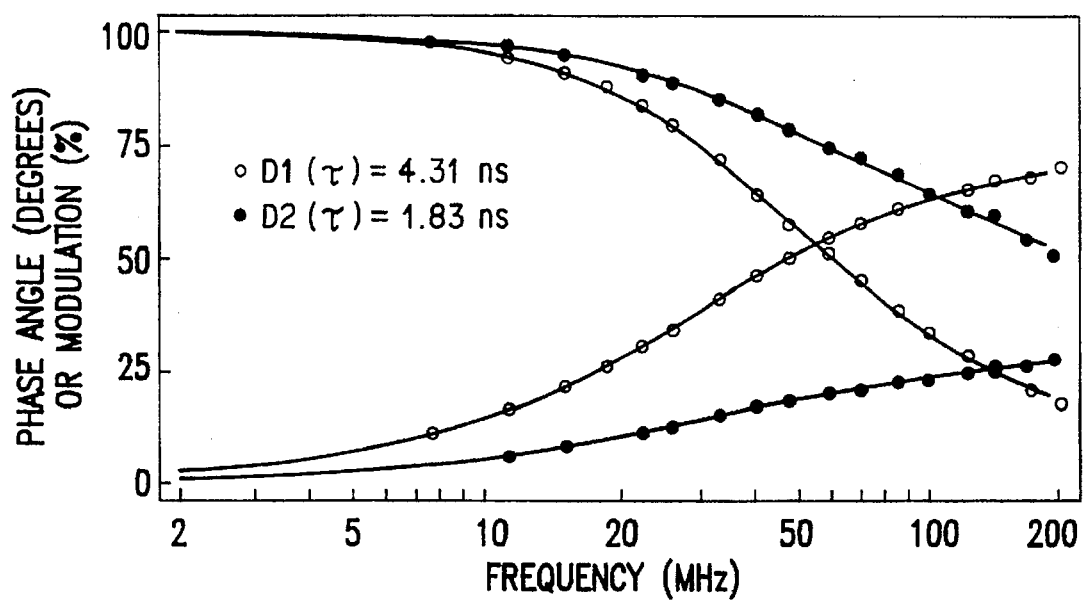
FIGS. 9A–9C are a graphical representation of modulation frequency versus phase angle and modulation factor for the donor-acceptor pair Texas Red-Bromothymol Blue.
Figure 9B:
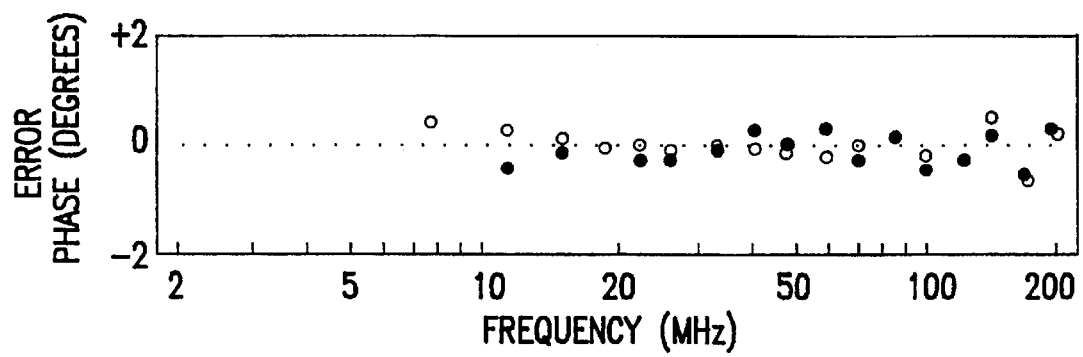
Figure 9C:
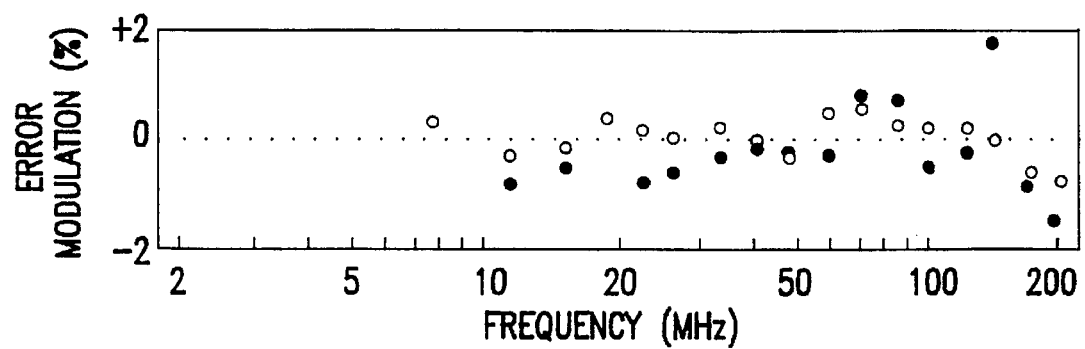

The frequency response of the donor alone and the donor with the lower acceptor concentration were measured, as shown in FIG. 9. As in the previous examples, the frequency responses were measured with 560 nm excitation using an R6G dye laser and a 600 nm interference filter for emission at 25° C. The samples were maintained with 100% humidity.

As can be seen in FIG. 9, as the frequency increases, the phase angle increases and the modulation factor decreases, although somewhat more dramatically than in Example 1. As in Example 2, the acceptor has a significant effect on the frequency response of the donor.

As in the previous examples, the donor was excited with a green acousto-optically modulated HeNe laser. The carbon dioxide concentration responses shown in FIGS. 10 and 11 were measured at a selected frequency of 133 MHz. Samples were equilibrated with $CO_2/N_2$ mixtures from a two-tube gas blender with a high accuracy measuring valve.

As can be seen from FIGS. 10 and 11, for the donor-acceptor pair Texas Red-Bromothymol Blue, as the concentration of carbon dioxide increases, the relative phase angle also increases, while the modulation factor decreases, to a greater degree than in the other examples.

The above is for illustrative purposes only. Modifications can be made within the scope of the invention as defined by the appended claims.

What is claimed is:

1. A method of optically determining concentration of analyte in a sample to be analyzed, said analyte in said sample being hydrogen ions or carbon dioxide, said method comprising the steps of:

contacting an energy transfer donor-acceptor pair with said analyte in said sample to be analyzed, wherein energy transfer between donor and acceptor of the pair is affected by the pH or carbon dioxide concentration of the sample, wherein the donor of the donor-acceptor pair is photoluminescent metal-ligand complex donor, and wherein photoluminescent lifetime of the probe is affected by said analyte;

exciting the sample with radiation;

detecting the resulting emission; and performing a calculation consisting essentially of calculating apparent luminescence lifetime of the emission to determine the pH or carbon dioxide concentration of the sample, wherein the lifetime is calculated using phase-modulation fluorometry or time-resolved fluorometry.

2. The method of claim 1, wherein the acceptor of the donor-acceptor pair is sensitive to the pH or $pCO_2$ of the sample.

3. The method of claim 1, wherein the acceptor is selected from the group consisting of Phenol Red, water-soluble Phenol Red and Bromothymol Blue.

4. The method of claim 1, wherein the donor and acceptor are linked via a spacer and are present in a known ratio.

5. The method of claim 1, wherein the donor and acceptor are bound to a carrier.

6. The method of claim 5, wherein the donor and acceptor are covalently bound to a polymeric carrier.

7. The method of claim 6, wherein the carrier is a hydrogel.

* * * * *